(12) United States Patent
Breeding et al.

(10) Patent No.: US 12,403,162 B2
(45) Date of Patent: *Sep. 2, 2025

(54) USE OF HEMOLYMPH OR HEMOLYMPH COMPONENTS FOR THE TREATMENT AND PREVENTION OF INFLAMMATION AND DRY SKIN

(71) Applicant: Marin Brands Inc., South Portland, ME (US)

(72) Inventors: William Patrick Breeding, South Portland, ME (US); Robert Bayer, Orono, ME (US)

(73) Assignee: Marin Brands Inc., South Portland, ME (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/121,292

(22) Filed: Dec. 14, 2020

(65) Prior Publication Data
US 2021/0177913 A1  Jun. 17, 2021

Related U.S. Application Data

(60) Provisional application No. 62/948,240, filed on Dec. 14, 2019.

(51) Int. Cl.
| | |
|---|---|
| *A61K 35/612* | (2015.01) |
| *A61K 35/618* | (2015.01) |
| *A61K 35/63* | (2015.01) |
| *A61K 38/17* | (2006.01) |
| *A61P 17/06* | (2006.01) |
| *A61K 9/00* | (2006.01) |

(52) U.S. Cl.
CPC .......... *A61K 35/612* (2013.01); *A61K 35/618* (2013.01); *A61K 35/63* (2015.01); *A61K 38/1767* (2013.01); *A61P 17/06* (2018.01); *A61K 9/0014* (2013.01)

(58) Field of Classification Search
None
See application file for complete search history.

(56) References Cited

U.S. PATENT DOCUMENTS

| | | |
|---|---|---|
| 8,436,141 B2 | 5/2013 | Becker |
| 9,078,906 B2 | 7/2015 | Bayer |
| 2011/0033499 A1 | 2/2011 | Cuthbertson |
| 2014/0234378 A1* | 8/2014 | Bayer .................... A61K 35/64 424/278.1 |

FOREIGN PATENT DOCUMENTS

| | | | | |
|---|---|---|---|---|
| FR | 2641463 A1 | * | 3/1991 | |
| FR | 2741266 A1 | * | 5/1997 | ............. A61K 38/17 |
| FR | 2804320 A1 | * | 8/2001 | ........... A61K 8/0212 |
| WO | WO-2005108576 A1 | * | 11/2005 | ....... C07K 14/43509 |

OTHER PUBLICATIONS

Medzhitov R. (2008) Origin and physiological roles of inflammation. Nature 454: 428-435. Jul. 14, 2008 (Year: 2008).*
FR-2804320-A1 translated doc (Year: 2001).*
FR2641463A1 translated doc (Year: 1991).*
Correale (Atopic Dermatitis: A Review of Diagnosis and Treatment, Am Fam Physician, 1999;60(4):1191-1198) retrieved on Feb. 22, 2024. (Year: 1999).*
Guo, D., et al. "Functional properties of hemocyanin from Oncomelania hupensis, the intermediate host of Schistosoma japonicum," Experimental Parasitology vol. 123, Issue 3, Nov. 2009, pp. 277-281.
Idakieva, K., et al. "Purification of Hemocyanin from Marine Gastropod *Rapana thomasiana* using Ammonium Sulfate Precipitation Method," Biotechnology & Biotechnological Equipment (2009), 23:3, pp. 1364-1367.
Keller, H., et al. "Abalone (*Haliotis tuberculata*) hemocyanin type 1 (HtH1)," Eur. J. Biochem. (1999) 264: pp. 27-38.
Molon, et al. "Molecular heterogeneity of the hemocyanin isolated from the king crab *Paralithodes camtschaticae*," Eur. J. Biochem. (2000) 267: pp. 7046-7057.
Pan, J.Y., et al. "Dodecamer is Required for Agglutination of Litopenaeus vannamei Hemocyanin with Bacterial Cells and Red Blood Cells," Marine Biotechnology (2008) 10(6), pp. 645-652.
Zanjani, et al. "Formulation of abalone hemocyanin with high antiviral activity and stability," European Journal of Pharmaceutical Sciences (2014) 53(1), pp. 77-85.
Mintel, "Energising Under Eye Cream" XP093200942, Database accession No. 1644605 [online] (Oct. 24, 2011) http://www.gnpd.com.

* cited by examiner

*Primary Examiner* — Terry A McKelvey
*Assistant Examiner* — Jacob A Boeckelman
(74) *Attorney, Agent, or Firm* — Amin Wasserman Gurnani LLP; George M. Carrera, Jr.; José J. Aparicio

(57) ABSTRACT

Uses are described for hemolymph, contents of hemolymph, fragments or components of the contents found within hemolymph, including hemocyanin, any of which may be derived from crustaceans, as functional agents to treat diseases, provide symptomatic relief, provide a beautifying or relieving effect to the intended organ or site-of-intended-use, or be used as an ingredient in formulations designed to aid in the relief of pathologies or states commonly associated with inflammation and dry skin, including, but not limited to eczema, dermatitis, psoriasis, cystitis, asthma, sinusitis, joint pain, as well as other instances of acute and chronic inflammation, and for relief of general symptoms that may be associated with inflammation and dry skin but not linked directly in the intended use, including, but not limited to, redness, itchiness, irritation, muscle or joint fatigue, swelling, hydrating the skin, and reducing transepidermal water loss (TEWL).

18 Claims, No Drawings

USE OF HEMOLYMPH OR HEMOLYMPH COMPONENTS FOR THE TREATMENT AND PREVENTION OF INFLAMMATION AND DRY SKIN

This application claims the benefit of U.S. Provisional Application No. 62/948,240, filed on Dec. 14, 2019, which is hereby incorporated by reference herein in its entirety.

TECHNICAL FIELD

The present invention relates to the use of or administration of hemolymph, or a component of hemolymph, in cosmetics, skincare, supplements, nutrition, pharmaceutical drugs and healthcare, for the general reduction of inflammation, and the hydration or prevention of transepidermal moisture loss from mammalian skin.

BACKGROUND

The use of naturally-derived compounds in fields such as cosmetics, nutrition and healthcare has been of rising interest. The prospect of new ingredients sourced from marine environments offers a wide range of abundance and possibility for multi-faceted ingredient function. Marine-derived compounds including proteins, peptides, carbohydrates and bacterial strains found in plants and animals have recently seen a significant amount of activity in these fields, with compound sources providing an abundance of availability, clinical studies revealing increasingly more potential to increase mammalian health, and the general populations' attitude toward natural and sustainable products becoming increasingly more favorable.

One untapped source of potential is that of the arthropod and mollusk family, with entire fishing industries dedicated to the catch and sale of meat derived from these sources, which produce immense amount of waste, as components not converted into viable products and sold into market are commonly disposed of in landfills or feed back into the environment. In many cases, the waste-byproducts of the processes offer an array of commercially viable applications beneficial to our society's needs. This potential is often not taken advantage of due to inability of the producer of traditional goods to realize such value-added opportunities, the inability of the producer to implement a viable process to convert these byproducts into value-added products, or the general lack of scientific exploration into such value-added opportunities to understand that they exist. It is believed that one of these untapped sources of potential lies in the use of hemolymph, or components of hemolymph, derived from arthropods or mollusks.

Hemolymph is a natural substance derived from arthropods and mollusks including lobsters, crabs, and oyster species. Certain formulations are known which contain hemolymph, or a glycoprotein found within the hemolymph, called hemocyanin for various uses.

One industry, with waste materials abundant and ripe for innovation, is the lobster industry. The lobster industry brings in millions of pounds of lobster per year in areas around the world, predominantly along North America's east coast—with Maine lobstermen bringing in over 119 million pounds of meat in 2018. In the processing of these lobsters, the meat is the primary component of interest, with other components such as the shell and hemolymph viewed as waste. It is estimated that at this volume of catch, between 1-5 million pounds of hemolymph is wasted, trickling down the drain, each year.

Similar industries involving the growth of catch of marine organisms such as oyster farming in the state of Maine, are growing at promising rates, offering additional streams of hemolymph that have potential, due to variance in biochemical structure, to possess superior strength in applications in comparison to hemolymph, or hemolymph components, from other marine sources. Organisms that are invasive and harmful to marine environments, such as the green crab, also offer streams of hemolymph, which if a strong enough commercial application of the hemolymph existed, could encourage the establishment of processes to collect it, which could yield a high-value product that simultaneously results in the safety and preservation of marine environments. Thus, it is clear that hemolymph from such sources should be explored and value-added applications, such as the ones described in this patent, be validated, documented and commercialized.

Skin conditions falling under the umbrella of complications with inflammation, hydration, and dryness afflict an overwhelming majority of the world's population. Whether due to lifestyle, diet, exercise, atmosphere, hormones, stress, genes, topical irritants, allergies or otherwise, conditions ranging from eczema and psoriasis to general issues with skin hydration and inflammation are on the rise. Current modalities suitable to address such conditions from the therapeutic to cosmetic level include ingredients such as topical steroids, which act aggressively to spot-treat skin but often cause further damage, to basic moisturizers and emollients that serve as mildly effective forms of maintenance but not effective, long-term solutions for troubled skin.

Thus, what is needed in the field is an alternative to limited bland ingredients, that does not cause the adverse effect of a harsh ingredient such as a topical steroid, that possesses the multifaceted capabilities to deliver therapeutic, symptomatic relief and cosmetic effects necessary to address conditions that often present as an amalgam of symptoms or complications. By leveraging one or more of the capabilities of hemolymph, or component within the hemolymph, to reduce inflammation and hydrate or reduce transepidermal moisture loss from dry skin, beneficial therapeutic or cosmetic effects may be realized in a mammalian subject.

SUMMARY OF THE INVENTION

In one embodiment, the present disclosure provides a novel use of arthropod hemolymph, and components thereof, as an ingredient or the active ingredient independently or mixed in formulations administered by way of parenteral, oral, nasal, ocular, transmucosal, and transdermal routes, to deliver a cosmetic, symptomatic relief, pharmaceutical drug, nutritional or general benefit to mammalian health. The invention relates to preparations, intended uses, formulations, intended outcomes as a result of use, of hemolymph, or components thereof, rendered preferably, but not exclusively, from lobsters, oysters, crabs or mollusks.

This technology provides a chemical composition comprising a marine ingredient with the capabilities of reducing mammalian inflammation, and hydrating mammalian skin, or reducing transepidermal moisture loss, i.e. transepidermal water loss (TEWL), from mammalian skin.

The hemolymph, hemocyanin or moiety found within hemolymph is able to perform as a gentle and effective alternative to existing treatment or cosmetic options due to its multi-faceted mechanisms of action working in unison together to delivered the desired activity relating to the reduction of inflammation and enhancing skin hydration or reducing transepidermal moisture loss properties in any or all therapeutic, symptomatic relief or cosmetic applications. Additionally, as opposed to many common treatment and cosmetic alternatives, the hemolymph, hemocyanin or moiety found within hemolymph is a gentle alternative as it does not cause adverse irritation or create withdrawal symptoms after discontinuing use.

A method for treating or preventing inflammation in a mammal is described, comprising the steps of: (a) providing a composition comprising hemolymph or a moiety found in hemolymph; and (b) administering the composition to the mammal. In a preferred embodiment, the composition is a topical composition administered topically to the skin.

A further method for treating or preventing dry skin in a mammal is described, comprising the steps of: (a) providing a composition comprising hemolymph or a moiety found in hemolymph; and (b) administering the composition to the mammal. In a preferred embodiment, the composition is a topical composition administered topically to the skin.

DETAILED DESCRIPTION

This invention relates to the use of hemolymph, hemocyanin, or other moieties found within hemolymph from arthropods, mollusks and recombinantly produced versions of such moieties, having the capability of reducing inflammation, hydrating skin or reducing transepidermal moisture loss from skin, used for the purpose of providing therapeutic, symptomatic relief and/or cosmetic effects to a mammal.

This invention further comprises the administration of hemolymph, a moiety found in hemolymph, a fragment or component of said moiety including but not limited to (preferably) the glycoprotein called hemocyanin, or peptides, used for the purpose of providing therapeutic, symptomatic relief, and/or cosmetic effects to a mammal, by leveraging one or more of the capabilities of reducing inflammation, hydrating skin or reducing transepidermal moisture loss from skin.

In one aspect, the development, and developed viable products, using hemolymph and hemolymph components found in the lobster as an ingredient, or the active ingredient, in cosmetic, skincare, supplements, nutritional supplements and products, pharmaceutical drugs and general healthcare applications, is described. Through investigational preliminary laboratory data and anecdotal evidence supporting the feasibility of these applications, it is believed 1-5 million of pounds of hemolymph, and components found within the hemolymph, can be converted into high-value ingredients and products to provide industries such as the lobster industry with a significantly value-added revenue stream.

Hemolymph may be extracted following a variety of procedures. In a preferred embodiment, hemolymph may be obtained from lobsters as mentioned in U.S. Pat. No. 9,078,906 B2, herein incorporated by reference. U.S. Pat. No. 9,078,906 describes use of hemolymph for antiviral and antineoplastic applications.

The form of hemolymph, or component of hemolymph, used in such products, can vary greatly. Numerous components found within the hemolymph have been shown to possess medicinal applications, such as the hemocyanin or peptides, which could give rise to motivation for using the hemolymph in its naturally-derived state, or isolating such components for more specific use.

In certain preferred embodiments, the components within the hemolymph, such as hemocyanin or peptides, may be isolated or purified in some manner. For components such as hemocyanin or peptides, this may occur using an array of typical purification methods, including, but not limited to, a form of chromatography such as affinity, high pressure liquid, ion-exchange or gel-filtration chromatography, dialysis, electrophoresis methods such as gel or two-dimensional electrophoresis, SDS-PAGE, precipitation, 'salting out', isoelectric focusing, immunoblotting, centrifugation, ultracentrifugation, enzymatic cleavage or solid-phase extraction.

Hemolymph, or hemolymph components, as derived naturally or from their respective isolation or purification techniques, could be incorporated into a formulation in crude form as-is, or further cleared of debris or contaminants with any known filtration technique, or converted from liquid to powder form using a process such as lyophilization, or combined with an array of ingredients to complement the efficacy, stability or other properties relating to a preferred use as a product.

The method of hemolymph component purification is certainly tailored to the component of interest, and the method may vary depending on intended component use; however, the true novelty does not lie in the isolation or purification process, rather, the preferred use of the component.

The hemolymph, hemocyanin or other moiety found within hemolymph may be administered independently (just the hemolymph, hemocyanin, or said moiety) or in a chemical composition, which may be delivered to a mammal via any mechanism of delivery.

The hemolymph, hemocyanin or other moiety found within hemolymph used may be obtained through natural (collected from an arthropod or mollusk) or recombinant (produced via culture in bioreactor) means. Such sources, from arthropods and mollusks, may include but are not limited to lobsters, crabs, oysters and mollusks, such as lobster species *Nephrops novegicus*, *Homarus gammarus*, *Panularis elephas* and *Homarus americanus*, as well as oyster species *Crassostrea virginica* and *Ostrea edulis*, crab species *Carcinus maenas*, *Portunus pelagicus*, *Portunus trituberculatus*, *Callinectes sapidus*, *Cancer pagurus*, *Metacarcinus magister* and *Chionoecetes*, crawfish species *Procambarus clarkii* and *Procambarus zonangulus*, shrimp species *Penaeus monodon*, *Pandalus borealis*, *Acetes japonicus* and *Trachysalambria curvirostris*, and mollusk classes gastropoda, bivalvia and cephalopoda.

The hemolymph, hemocyanin or other moiety found within hemolymph may be used as naturally obtained from the natural or recombinant source (un-modified form), an isomer, subunit, component, or fragment of hemocyanin, a functionalized form, a modified form, a glycosylated form, a form resuspended in a physiologically acceptable buffer or lyophilized form, or prepared in any other method.

One preferred way to practice the invention is to incorporate the hemolymph, hemocyanin or moiety found within hemolymph to a composition as a delivery vehicle for topical administration to mammalian skin.

Delivery System

Suitable dosage forms include tablets, capsules, solutions, suspensions, powders, gums, and confectionaries. Sublingual delivery systems include, but are not limited to, dissolvable tabs under and on the tongue, liquid drops, and beverages. Edible films, hydrophilic polymers, oral dissolvable films or oral dissolvable strips can be used. Other useful delivery systems comprise oral or nasal sprays or inhalers, and the like.

For oral administration, the compounds or extracts may be combined with one or more solid inactive ingredients for the preparation of tablets, capsules, pills, powders, granules or other suitable dosage forms. For example, the active agent may be combined with at least one excipient such as fillers, binders, humectants, disintegrating agents, solution retarders, absorption accelerators, wetting agents, absorbents, or lubricating agents. Other useful excipients include magnesium stearate, calcium stearate, mannitol, xylitol, sweeteners, starch, carboxymethylcellulose, microcrystalline cellulose, silica, gelatin, silicon dioxide, and the like.

Further for oral administration, the compounds or extracts may be incorporated with an excipient and used in the form of ingestible tablets, buccal tablets, troches, capsules, elixirs, suspensions, syrups, wafers, and the like. The tablets, troches, pills, capsules, and the like can also contain the following: a binder such as gum tragacanth, acacia, corn starch, or gelatin; excipients such as dicalcium phosphate; a disintegrating agent such as corn starch, potato starch, alginic acid, and the like; a lubricant such as magnesium stearate; and a sweetening agent such as sucrose, lactose, or saccharin can be added or a flavoring agent such as peppermint, oil of wintergreen, or cherry flavoring. When the dosage unit form is a capsule, it can contain, in addition to materials of the above type, a liquid carrier. Various other materials can be present as coatings or to otherwise modify the physical form of the dosage unit. For instance, tablets, pills, or capsules can be coated with shellac, sugar, or both. A syrup or elixir can contain the active compound, sucrose as a sweetening agent, methyl and propylparabens as preservatives, a dye, and flavoring such as cherry or orange flavor. Oil-in-water emulsions may be better suited for oral use in infants because these are water-miscible, and thus their oiliness is masked. Such emulsions are well known in the pharmaceutical sciences.

Routes of Administration

The compounds or extracts may be administered by any route, including but not limited to oral, sublingual, buccal, ocular, pulmonary, rectal, and parenteral administration, or as an oral or nasal spray (e.g. inhalation of nebulized vapors, droplets, or solid particles). Parenteral administration includes, for example, intravenous, intramuscular, intraarterial, intraperitoneal, intranasal, intravaginal, intravesical (e.g., to the bladder), intradermal, transdermal, topical, or subcutaneous administration. Also contemplated within the scope of the invention is the instillation of hemolymph in the body of the patient in a controlled formulation, with systemic or local release of the drug to occur at a later time. For example, the drug may be localized in a depot for controlled release to the circulation, or for release to a local site of a growth or area of concern.

Regardless of application; therapeutically used to address a pathology, to mitigate symptoms, or for cosmetic effects, the composition may be comprised of a number of additional ingredients that provide complementary or supplementary effects, and delivered through any vehicle and method desired. Potential delivery mechanisms include, but are not limited to parenteral, oral, transmucosal, transdermal or topical routes; via intravenous, subcutaneous, intrathecal, intramuscular or site-specific ingestion routes, as a solution, suspension or emulsion, liquid suspension, physical mixture, encapsulated liquid suspension, encapsulated physical mixture, spray, topical liquid, emulsion, suspension, ointment, encapsulation, gelling systems, micelle, dendrimer, liposome, nanoparticle or time delivery system, dendrimers, liposomes, rectally, vaginally, buccally, or applied to the skin as a gel, cream, ointment, powder, emulsion, paste, spray, suspension, foaming agent, serum, shampoo, wax, balm, emollient, oil, lotion, band-aid, patch-test or suspended within an encapsulation.

In an embodiment, the invention relates to a chemical composition comprising at least hemolymph, a moiety found in hemolymph, a fragment or component of said moiety including but not limited to (preferably) hemocyanin or peptides, having the capability of reducing inflammation, hydrating skin or reducing transepidermal moisture loss from skin, used for the purpose of providing therapeutic, symptomatic relief and/or cosmetic effects to a mammal.

The hemolymph or moiety (glycoprotein, hemocyanin) found within hemolymph used may be obtained through natural (collected from an arthropod or mollusk) or recombinant (produced via culture in bioreactor) means, as discussed herein, and may be used in a composition.

In a therapeutic embodiment, the composition may be used to address pathologies relating to inflammation, skin hydration, or loss of skin moisture content, or used for treatment modalities for the purpose of indirectly addressing a pathology. Such pathologies may include general dermatitis, atopic dermatitis, allergic contact dermatitis, seborrheic dermatitis, radiation dermatitis, radiation exposure irritation, xerosis, perioral dermatitis, stasis dermatitis, pregnancy-induced dermatitis, perineal dermatitis, autoimmune disorders, eczema, psoriasis, rosacea, pruritus, acne, rashes, contact burns, cuts, fungal skin infections, bacterial skin infections, vitiligo, inflammatory bowel disease, coeliac disease, alopecia areata, hives, sunburns, photoallergic skin reactions, abnormal scarring keloids, asthma, cystitis, sinusitis, transplant rejection, occupational inflammatory or dry skin conditions, dermopathy, cercarial dermatitis, lichen planus, incision inflammation, irritation or redness care and post-surgical inflammation, redness or irritation incision care.

In a symptomatic relief embodiment, the composition may be used to relieve or modulate symptoms directly or indirectly associated with a host of inflammatory or dry skin conditions as described; symptoms commonly associated with inflammatory conditions, including erythema, papules, erosion, exudation, itching, redness, swelling, fatigue, joint stiffness, joint pain, drug rash, heat rash, intertrigo and diaper rash.

The composition made in accordance with the embodiments herein may also address symptoms commonly associated with abnormalities in skin hydration, including decreasing transepidermal moisture loss, binding moisture, increasing skin moisture content, altering sebum production, and decreasing skin dryness.

A third embodiment involves the use of the chemical composition for delivering a range of cosmetic effects. These cosmetics effects highly overlap with those of the symptom management applications, functions which may be interchanged between symptomatic relief and cosmetic purposes, including soothing, calming, calming aggravated, sensitive, troubled, 'angry', 'upset' or irritated skin, relieving, redness reducing, helping skin retain moisture, combatting dehydration, or acting as a humectant.

The material used in a composition made in accordance with the embodiments herein may be used as naturally obtained from the natural or recombinant source (un-modified form), an isomer, subunit, component, or fragment of hemocyanin, a functionalized form, a modified form, a glycosylated form, a form resuspended in a physiologically acceptable buffer or lyophilized form, or prepared in any other method.

Regardless of application; therapeutically used to address a pathology, to mitigate symptoms, or for cosmetic effects, the composition may be comprised of a number of additional ingredients that provide complementary or supplementary effects, and delivered through any vehicle and method desired. Potential delivery mechanisms include, but are not limited to Parenteral, Oral, Transmucosal, Transdermal/Topical routes; via intravenous, subcutaneous, intrathecal, intramuscular or site-specific ingestion routes, as a solution, suspension or emulsion, liquid suspension, physical mixture, encapsulated liquid suspension, encapsulated physical mixture, spray, topical liquid, emulsion, suspension, ointment, encapsulation, gelling systems, micelle, dendrimer, liposome, nanoparticle or time delivery system, dendrimers, liposomes, rectally, vaginally, buccally, or applied to the skin as a gel, cream, ointment, powder, emulsion, paste, spray, suspension, foaming agent, serum, shampoo, wax, balm, emollient, oil, lotion, band-aid, patch-test or suspended within an encapsulation.

Hemolymph extracts or fractions are useful for the present invention.

Process for Preparing Hemocyanin Active Ingredient (Natural Hemocyanin)

In one embodiment, the hemocyanin may be obtained from a natural source (e.g. from arthropods), and prepared in a method, as follows.

The hemolymph of the arthropod is collected via vacuum or gravity feed into a holding container. This can be accomplished in a number of ways; the arthropod or mollusk, preferably lobster, can be lanced in easily penetrable or soft areas, including across the abdomen area adjacent to the swimmerets, allowing for hemolymph to drain, a needle may be inserted to allow for hemolymph to gravimetrically drain or be vacuum drained, the lobster may be placed on an mechanical or stationary lancing and flow system that lances the underbelly and directs hemolymph flow into a basin, the lobster abdomen may be separated from the thorax, as performed in traditional seafood processing, and the resulting hemolymph flow draining out may be directed into a basin.

The preferred methods of hemolymph collection are via vacuum system, using a sterilized 16 gauge needle attached to a tube which feeds into a collection basin, drawing hemolymph at a rate between 80-160 mL/min. Additionally, it is preferred to use an automated or stationary lancing and flow system, where the lobster may be manually lanced by an operator using a needle or sharp edge and placed onto a holder which allow hemolymph to flow and directs said flow into a collection basin, or, the operator may place the lobster on the holder, which employs a stationary or mechanically actuated lancing needle or sharp edge, thus allowing for full automation of the lancing and hemolymph flow into basin process. Finally, a third preferred method of hemolymph collection simply involves the use of a needle attached to a temporary collection vessel, such as a syringe or tube attached to a bulb, to draw the hemolymph from the lobster and subsequently deposit the hemolymph into a storage basin.

The collected hemolymph can be immediately stored in a −20° C. freezer (to be later thawed and subjected to the following step), allowed to sit in ambient conditions for no longer than two hours, in which the hemolymph clotting cascade naturally forms layers of clotted cellular mass/debris and a hemocyanin rich liquid layer, or the hemolymph is immediately subjected to chemical or physical perturbation to further activate the clotting cascade and expedite the formation of the solid and liquid layers.

Once the solid and liquid layers are formed, they may then be separated via centrifugation and decanting the liquid layer, filtration (vacuum, flow, gravimetric through a membrane, porous material, filter, etc) to isolate the liquid layer, siphoning, draining, or another form of separation to remove the solid layer and isolate the liquid, hemocyanin-rich layer.

Preferably, the solid layer is filtered out by gravimetric or vacuum flow through a 0.22-40 µm filter, allowing the filter to remove the large solid particulates in solid phase, resulting in a clear, hemocyanin-rich liquid phase.

An additional preferable method to isolate the hemocyanin-rich liquid phase may be to centrifuge the hemolymph at between 1,000 g-12,000 g for between 5-60 minutes at a temperature between 4-20° C., and decant the supernatant to obtain the hemocyanin-rich liquid layer.

The concentration of hemocyanin suspended in the resulting hemocyanin-rich liquid layer may be of interest and can be assessed by any normal means of measuring protein concentration. Preferably, absorbance, refractometry and the Bradford assay are used to measure protein concentration. Hemocyanin, regardless of the source, displays unique absorbance bands are 280 nm and 350 nm. If absorbance is used, the 280 nm is the most accurate and reliable measure of concentration, as the 350 nm peak may vary depending on the degree of oxygenation of hemocyanin in solution. Therefore, more preferably, refractometry may be used to assess hemocyanin concentration by way of estimation of total protein content. Hemocyanin, depending on the source, accounts for between 90-99.9% of the total protein content, therefore refractometry is a simple high-level means of assessment. Finally, the Bradford assay may be used to measure protein content, following a standard procedure to measure concentration.

With the hemocyanin-rich layer isolated, a number of steps may be performed based on the required degree of standardization and purification of the end ingredient used in a composition.

In one embodiment, the hemocyanin-rich liquid layer may be used as obtained from the filtration step, where the protein content of the hemocyanin-liquid layer obtained from filtration is generally 90-99.9% hemocyanin.

In another embodiment, the hemocyanin-rich liquid may be subjected to lyophilization to obtain a dried form of the solution components, primarily being hemocyanin. One may elect to add a sugar to the hemocyanin-rich liquid to enhance protein thermal stability, thus decreasing the likeliness of denaturing and unfolding during the freezing and dehydration process. Preferably, sucrose or trehalose are added to the solution, at an amount of 10-800% 10-800% w/w sugar to hemocyanin, ideally 20-80% sucrose w/w hemocyanin and 50-600% trehalose w/w hemocyanin. However, it is possible for the hemocyanin-rich layer to be lyophilized without the addition of a sugar. The solution should be lyophilized for at least 8 hours and can be performed at a range of temperatures preferably between −80° C. and −50° C. (Zanjani, et al., Formulation of abalone hemocyanin with high antiviral activity and stability, European Journal of Pharmaceutical Sciences (2014) 53(1), 77-85. https://doi.org/10.1016/j.ejps.2013.11.013).

In a third embodiment, the hemocyanin-rich liquid layer may be diluted based on the concentration of hemocyanin in solution, to meet a concentration standard set by those preparing the end composition. In an example, the hemocyanin-rich liquid layer may be diluted in distilled water, saline, PBS or another solution commonly used in cosmetics and biotechnology, preferably a physiologically acceptable, non-toxic, non-irritating solution.

In a fourth embodiment, the hemocyanin may be further purified to remove or isolate the protein from the liquid layer. To do so, a number of physical and chemical separation methods may be employed to remove the protein from solution, including centrifugation, ultracentrifugation, precipitation, filtration, chromatography or any other physical or chemical method to isolate the protein from solution.

Precipitation, also referred to as 'salting out' is one preferred method of hemocyanin purification, as the method, especially considering the utilization of ammonium sulfate, is ideal for use in scaling up and large-scale purification, being relatively simple, cost-effective, and allowing for large, continuous quantities of raw material to be purified. While an array of salts may be used, ammonium sulfate is preferred for a precipitation procedure. Following a simple method described by Nichols et al., and well known in the field of protein purification, ammonium sulphate crystals can be continuously added to hemocyanin-rich solution an stirred over a period of 12 hours, at 4 C, to reach 50% ammonium sulphate saturation, followed by centrifuging the solution at 10,000 rpm at 4° C. for one hour, decanting, resuspending the pellet and repeated 2-3 times to ensure purity. Following this, the solution was dialyzed against a suitable stabilizing buffer to remove ammonium sulfate and obtain hemocyanin in solution, and finally filtered with a 0.22-0.4 µm filter to sterilize (K. Idakieva, et al. Purification of Hemocyanin from Marine Gastropod Rapana Thomasiana using Ammonium Sulfate Precipitation Method, *Biotechnology & Biotechnological Equipment* (2009) 23:3, 1364-1367, DOI: 10.1080/13102818.2009.10817671).

Ultracentrifugation may also be used to isolate the hemocyanin from the hemocyanin-rich liquid, following a simple procedure of centrifuging the solution between 20,000-80,000 rpm, preferably between 30,000-50,000 rpm, at 5° C. for a timespan between 1-18 hours (Guo, D., et al. Functional properties of hemocyanin from Oncomelania hupensis, the intermediate host of Schistosoma japonicum. *Experimental Parasitology* (2009) 123(3), 277-281; Keller, H., et al. Abalone (*Haliotis tuberculata*) hemocyanin type 1 (HtH1), *Eur. J. Biochem*. (1999) 264: 27-38).

While precipitation may be an ideal method to isolate the hemocyanin from an economic, scale and simplicity standpoint, the hemocyanin may be purified through a number of different means, including SDS-PAGE, gel or affinity chromatography, HPLC and other forms of protein purification, all of which have been fairly explored in the isolation of hemocyanin from various crustaceans by numerous research groups, and can be performed using standard procedures by those well versed in the art of protein purification.

Regardless of the purification step, once the hemocyanin is isolated (if such a series of steps is desired for use), it may be resuspended in another solution commonly used in cosmetics and biotechnology, including saline, PBS, or preferably another physiologically acceptable, non-toxic, non-irritating solution. Additionally, the hemocyanin may be subjected to lyophilization following the previously mentioned lyophilization procedure obtain a dried, solid form.

The purity of the resulting hemocyanin may be assessed using SDS-PAGE, gel chromatography, TEM, Western Blot, absorption spectroscopy and other analytical techniques commonly practiced in the field of protein purification and characterization, following standard procedures. In chromatography procedures, as hemocyanin is most abundant in the lobster as a ~75 kDa protein, it is recommended that standards such as ovalbumin, beta-galactosidase and ovotransferrin are used, having similar weights to the hemocyanin protein and thus allowing for close and accurate standards to compare to. For absorbance spectroscopy, as previously mentioned, 280 nm should be used to assess the concentration of hemocyanin, referencing an equation for concentration obtained by plotting Bradford assay concentration measurements against absorbance and relating the two measurements to a known concentration.

Additional steps may be employed to modulate or enhance the desired activity or efficacy of the hemocyanin, or hemocyanin-rich liquid, including obtaining a certain isoform, glycoform or subunit assemblies. As previously mentioned, sugars such as sucrose and trehalose may be added to the hemocyanin-rich liquid, or a solution of purified resuspended hemocyanin, to further glycosylate the protein, which may be advantageous both for enhanced thermal stability as well as enhanced efficacy in use cases including the reduction of inflammation, enhancement of hydration and prevention of transepidermal moisture loss properties.

In some cases, it may be of interest to isolate and utilize specific subunit arrangements of hemocyanin, in which a standard method to isolate the subunit may be followed, preferably using affinity chromatography or pH modulation as the simplest means to obtain either a single subunit, or the desired subunit aggregation state. The single lobster hemocyanin subunit is known to weigh roughly 75 kDa, often arranging as a monomer, and as hexamers and dodecamers.

Molon et al. showed how raising a hemocyanin-containing solutions' pH to 9 resulted in nearly 100% dissociation of hemocyanin aggregation states, therefore obtaining a solution of nearly 100% hemocyanin monomers (Molon, et al., Molecular heterogeneity of the hemocyanin isolated from the king crab Paralithodes camtschaticae, *Eur. J. Biochem*. (2000) 267: 7046-7057). Correspondingly, by lowering the pH and adding $Ca^{2+}$ resulted in the reassociation of the subunits into dodecamer and hexamer forms. Interestingly, Pan et al. demonstrated how between the dodecamer and hexamer, the dodecamer is primarily found in freshly pooled hemolymph, however, upon storing at 4° C. for 3 days, the hexamer became the main form, which evidently was more stable, suggesting that temperature may also be modulated to obtain the desired subunit aggregation state (Pan, J. Y., et al., Dodecamer is required for agglutination of Litopenaeus vannamei hemocyanin with bacterial cells and red blood cells, *Marine Biotechnology* (2008) 10(6), 645-652. https://doi.org/10.1007/s10126-008-9115-8).

It has been shown that hemocyanins that exhibit impressive polymorphism (in other arthropods) result in protein isoforms that better suited for certain healthcare or biotechnology applications. Additionally, numerous studies have linked hemocyanin glycoform, the specific type or extent of the protein glycosylation, to efficacy on a broad spectrum from pathology treatment to altering cosmetic appearances, which is of specific interest for cosmetic and dry skin applications, where glycoprotein degree of glycosylation plays a major factor in skin hydrating activity. Finally, the hemocyanin subunit arrangement from monomer to hexamer and dodecamers may result in altered efficacy depending on the specific use case and mode of delivery, therefore altering the pH or utilizing another separative technique to isolate the clusters of subunits in varying arrangements may be advantageous.

Therefore in this invention, what may be used as the 'active' or 'key' ingredient includes a hemocyanin-rich liquid obtained as naturally obtained from hemolymph, a hemocyanin-rich liquid diluted to a desired concentration, a hemocyanin-rich liquid containing the desired hemocyanin isoform, glycoform or subunit aggregation state, a purified hemocyanin isolated from the liquid in dried form or resuspended in a new solution, or a purified hemocyanin with desired isoform, glycoform or subunit aggregation state.

Process for Preparing Hemocyanin Active Ingredient (Recombinant Hemocyanin)

In another embodiment, the hemocyanin used for the described applications may be recombinantly produced via large scale bioreactor fermentation.

This can be accomplished following a standard recombinant protein production procedure. First, one must understand the DNA sequence that codes for the hemocyanin, or hemocyanin subunit of interest, and obtain the RNA from the original arthropod or mollusk source. A fragment can be cut and inserted into a suitable vector. This vector is introduced into a suitable host system (in vitro, *E. Coli*, Yeast, Mammalian Cell), and the system is transformed to express the DNA encoding for the desired hemocyanin or hemocyanin subunit. Following small scale tests to ensure the correct protein is expressed (measurable by simple and standard assays including ELISA and Western Blots) in the desired range of yield, production can be scaled up to fermentation in a large bioreactor.

Glycoproteins can be purified from solution by lysis of culture cells, centrifuging the solution and decanting the supernatant containing the glycoprotein. Presence, purity, concentration and other relevant information pertaining to the produced glycoprotein can analyzed using SDS-PAGE, gel chromatography, TEM, Western Blot, absorption spectroscopy and other analytical techniques commonly practiced in the field of protein purification and characterization.

Following the collection and purification of the resulting protein, again, additional steps may be taken to result in optimal isoforms or optimally glycosylated proteins, depending on the desired use case for the protein. A preferable modification to the resulting protein is glycosylation, which is more conveniently accomplished post-production as opposed to expression of the protein in a glycosylated form, or glycosylation in the reactor, where glycosylated forms of glycoproteins and hemocyanins have shown to possess enhanced efficacy related to various biomedical and cosmetic applications.

Thus, in these embodiments, the hemocyanin material used is a recombinant hemocyanin, or hemocyanin subunit, which may be further treated to shift the proteins towards a desired isoform, subunit assembly, or degree of glycosylation. This hemocyanin or hemocyanin subunit may be used as an active material that is suspended or resuspended in a desired solution or lyophilized and supplied in dried, powder form. In a preferred embodiment, a hemolymph containing formulation or composition may contain hemocyanin in a dosage or amount ranging from about 1.2 ng to about 472 mg.

The intended uses described herein range from cosmetic and nutritional products and supplements to products for mitigation of symptoms and pharmaceutical drugs, without limitation. Provided below are examples of patient diary data anecdotally documenting the result of using a topical formula containing hemolymph, for enhancing visual appearance and feeling of skin, and self-assessed mitigation of symptoms commonly associated with their self-assessed pathology.

In an embodiment, a hemolymph containing formulation may contain from about 0.05% by weight hemolymph or a moiety found in hemolymph, to about 20% by weight hemolymph or a moiety found in hemolymph, based on the total weight of the formulation.

Following are several initial test examples.

Eczema

Case 1: A young adult female with a manifestation of eczema applied to her flared-up facial areas a topical formulation comprised of 20% hemolymph by weight, hyaluronic acid, potassium sorbate, aloe barbadensis juice, prunus dulcis oil, emulsifying wax, stearic acid, glycerin, phenoxy-ethanol, tocopherol, persea americana oil, simmondsia chinensis oil, sheabutter, xanthan gum, lecithin, salix alba extract, azadirachta indica oil, carbomer, triethanolamine, rosmarinus officinalis oleoresin, tetrasodium EDTA and citric acid. She spot-treated the local eczema flare-ups numerous times throughout a typical day, as-needed, applying a dollop of formulation, effectively 1.25 grams of hemolymph per application, for a time period of 7 days. After this period, she experienced clearing of her eczema afflicted areas and associated symptoms of dryness, redness, itching, and inflammation.

Case 2: An middle-aged adult female with a manifestation of eczema applied to her flared-up hands a topical formulation comprised of 20% hemolymph by weight, hyaluronic acid, potassium sorbate, aloe barbadensis juice, prunus dulcis oil, emulsifying wax, stearic acid, glycerin, phenoxy-ethanol, tocopherol, persea americana oil, simmondsia chinensis oil, sheabutter, xanthan gum, lecithin, salix alba extract, azadirachta indica oil, carbomer, triethanolamine, rosmarinus officinalis oleoresin, tetrasodium EDTA and citric acid. She spot-treated the local eczema flare-ups numerous times throughout a typical day, as-needed, applying a dollop of formulation, effectively 1.25 grams of hemolymph per application, for a time period of 4 days. After this period, she experienced clearing of her eczema afflicted areas and associated symptoms of dryness, redness, itching, and inflammation.

Case 3: A young adult female with a manifestation of eczema applied to her flared-up face and arms a topical formulation comprised of 20% hemolymph by weight, hyaluronic acid, potassium sorbate, aloe barbadensis juice, prunus dulcis oil, emulsifying wax, stearic acid, glycerin, phenoxy-ethanol, tocopherol, persea americana oil, simmondsia chinensis oil, sheabutter, xanthan gum, lecithin, salix alba extract, azadirachta indica oil, carbomer, triethanolamine, rosmarinus officinalis oleoresin, tetrasodium EDTA and citric acid. She spot-treated the local eczema flare-ups numerous times throughout a typical day, as-needed, applying a dollop of formulation, effectively 1.25 grams of hemolymph per application, for a time period of 7 days. After this period, she experienced clearing of her eczema afflicted areas and associated symptoms of dryness, redness, itching and inflammation.

Case 4: A young male with a manifestation of eczema on his arms, legs and neck applied a topical formulation comprised of 20% hemolymph by weight, hyaluronic acid, potassium sorbate, aloe barbadensis juice, prunus dulcis oil, emulsifying wax, stearic acid, glycerin, phenoxy-ethanol, tocopherol, persea americana oil, simmondsia chinensis oil, sheabutter, xanthan gum, lecithin, salix alba extract, azadirachta indica oil, carbomer, triethanolamine, rosmarinus officinalis oleoresin, tetrasodium EDTA and citric acid. He spot-treated the local eczema flare-ups numerous times throughout a typical day, as-needed, applying a dollop of formulation, effectively 1.25 grams of hemolymph per application, for a time period of 4 days. After this period, he no longer experienced symptoms of dryness, redness, itching and inflammation.

Psoriasis

Case 1: An middle-aged adult female with a manifestation of psoriasis applied to her patch of psoriasis a topical formulation comprised of 20% hemolymph by weight, hyaluronic acid, potassium sorbate, aloe barbadensis juice, prunus dulcis oil, emulsifying wax, stearic acid, glycerin, phenoxy-ethanol, tocopherol, persea americana oil, simmondsia chinensis oil, sheabutter, xanthan gum, lecithin, salix alba extract, azadirachta indica oil, carbomer, triethanolamine, rosmarinus officinalis oleoresin, tetrasodium EDTA and citric acid. She spot-treated the local patch of psoriasis numerous times throughout a typical day, as-needed, applying a dollop of formulation, effectively 1.25 grams of hemolymph per application, for a time period of 3 days. After this period, she experienced clearing of her psoriatic area and associated symptoms of dryness, redness, inflammation and itching.

Acne

Case 1: A young adult female with mild to moderate acne applied to her acne a topical formulation comprised of 20% hemolymph by weight, hyaluronic acid, potassium sorbate, aloe barbadensis juice, prunus dulcis oil, emulsifying wax, stearic acid, glycerin, phenoxy-ethanol, tocopherol, persea americana oil, simmondsia chinensis oil, sheabutter, xanthan gum, lecithin, salix alba extract, azadirachta indica oil, carbomer, triethanolamine, rosmarinus officinalis oleoresin, tetrasodium EDTA and citric acid. She spot-treated the local eczema flare-ups numerous times throughout a typical day, as-needed, applying a dollop of formulation, effectively 1.25 grams of hemolymph per application, for a time period of 2 days. After this period, she experienced a reduction of redness and inflammation.

Example 1

Eczema 59 individuals with eczema, including Asian, African American, Hispanic, and White ethnicities, from toddler to 65+ age groups, topically applied a cream composition containing hemocyanin to areas of the body affected by an eczema flare up, including the Face, Neck, Scalp, Nose, Eyelid, Perioral, Armpit, Upper arm, Elbow, Forearm, Hand, Finger Stomach, Chest, Lower and Upper Back, Thigh, Shin, Knee, Feet areas. The composition contained Water (Aqua), Hemocyanin (Marine Glycoprotein), Butyrospermum Parkii Shea Butter Fruit, Cetyl Alcohol, Glyceryl Stearate, Glycerin, Caprylic/Capric Triglyceride, Sorbitan Oleate Decylglucoside Crosspolymer, Polyacrylamide, C13-14 Isoparaffin, Laureth-7, Cocos Nucifera (Coconut) Oil, Squalane, Tocopherol (Vitamin E), Hyaluronic Acid, Sodium Benzoate, Sodium Levulinate, Potassium Sorbate, Sodium Phytate. User experienced was assessed by subjective participant self-reporting, and responses were collected at times users were able to confidently self-report significant results, ranging between 1-7 days of cream usage. Of this group, 91% reported the cream felt soothing on the skin, significantly reduced itching, left the skin feeling significantly hydrated, visibly reduced dryness, visibly reduced the appearance of a flare up, visibly reduced redness, visibly reduced inflammation, and left the skin appearing visibly more healthy.

Example 2

Psoriasis 15 individuals with psoriasis, including Asian, African American, Hispanic, and White ethnicities, from toddler to 65+ age groups, topically applied a cream composition containing hemocyanin to areas of the body affected by psoriasis, including the Face, Scalp, Eyelid, Nose, Hand, Thigh, Knee. The composition contained Water (Aqua), Hemocyanin (Marine Glycoprotein), Butyrospermum Parkii Shea Butter Fruit, Cetyl Alcohol, Glyceryl Stearate, Glycerin, Caprylic/Capric Triglyceride, Sorbitan Oleate Decylglucoside Crosspolymer, Polyacrylamide, C13-14 Isoparaffin, Laureth-7, Cocos Nucifera (Coconut) Oil, Squalane, Tocopherol (Vitamin E), Hyaluronic Acid, Sodium Benzoate, Sodium Levulinate, Potassium Sorbate, Sodium Phytate. User experienced was assessed by subjective participant self-reporting, and responses were collected at times users were able to confidently self-report significant results, ranging between 1-7 days of cream usage. Of this group, 93% reported the cream felt soothing on the skin, significantly reduced itching, left the skin feeling significantly hydrated, visibly reduced dryness, visibly reduced redness, visibly reduced inflammation, visibly reduced the appearance of a flare up and left the skin appearing visibly more healthy.

Example 3

Dry, Aggravated Skin 47 individuals self-reporting dry, aggravated skin, including Asian, African American, Hispanic, and White ethnicities, from toddler to 65+ age groups, topically applied a cream composition containing hemocyanin to areas of the body exhibiting dry, aggravated skin, including the Face, Neck, Chest, Forearm, Hand, Finger, Thigh, Knee, Shin, Feet areas. User experienced was assessed by subjective participant self-reporting, and responses were collected at times users were able to confidently self-report significant results, ranging between 1-7 days of cream usage. The composition contained Water (Aqua), Hemocyanin (Marine Glycoprotein), Butyrospermum Parkii Shea Butter Fruit, Cetyl Alcohol, Glyceryl Stearate, Glycerin, Caprylic/Capric Triglyceride, Sorbitan Oleate Decylglucoside Crosspolymer, Polyacrylamide, C13-14 Isoparaffin, Laureth-7, Cocos Nucifera (Coconut) Oil, Squalane, Tocopherol (Vitamin E), Hyaluronic Acid, Sodium Benzoate, Sodium Levulinate, Potassium Sorbate, Sodium Phytate. Of this group, 91% reported the cream felt soothing and calming on the skin, significantly reduced itching and discomfort, left the skin feeling significantly hydrated, visibly reduced redness and dryness, calmed hands aggravated from excessive hand washing and sanitizing, mitigated dryness and inflammation from wind burn, wind rash, temperature and weather-induced dryness, and redness, visibly reduced inflammation, and left the skin appearing visibly more healthy.

Example 4

Rashes 8 individuals with rashes including poison ivy, brown tail moth rash and diaper rash, including White and Hispanic ethnicities, ranging from toddler to 65+ age groups, topically applied a cream composition containing hemocyanin to areas of the body affected by an itchy, inflamed rash, including the Face, Scalp, Neck, Hand, Finger, Forearm, Chest, Stomach, Back, Upper arm, Thigh, Knee, Shin and Feet areas. The composition contained Water (Aqua), Hemocyanin (Marine Glycoprotein), Butyrospermum Parkii Shea Butter Fruit, Cetyl Alcohol, Glyceryl Stearate, Glycerin, Caprylic/Capric Triglyceride, Sorbitan Oleate Decylglucoside Crosspolymer, Polyacrylamide, C13-14 Isoparaffin, Laureth-7, Cocos Nucifera (Coconut) Oil, Squalane, Tocopherol (Vitamin E), Hyaluronic Acid, Sodium Benzoate, Sodium Levulinate, Potassium Sorbate, Sodium Phytate. User experienced was assessed by subjective participant self-reporting, and responses were collected at times users were able to confidently self-report significant results, ranging between 1-7 days of cream usage. Of this group, 100% reported the cream felt soothing on the skin, significantly reduced discomfort, irritation and itching, visibly reduced redness and inflammation, and left the skin appearing visibly more healthy.

Example 5

Rosacea 3 individuals with rosacea, including White ethnicities, ranging from 25-65+ age groups, topically applied a cream composition containing hemocyanin to areas of the body affected by rosacea, including the Face, Back, Chest and Neck areas. The composition contained Water (Aqua), Hemocyanin (Marine Glycoprotein), Butyrospermum Parkii Shea Butter Fruit, Cetyl Alcohol, Glyceryl Stearate, Glycerin, Caprylic/Capric Triglyceride, Sorbitan Oleate Decylglucoside Crosspolymer, Polyacrylamide, C13-14 Isoparaffin, Laureth-7, Cocos Nucifera (Coconut) Oil, Squalane, Tocopherol (Vitamin E), Hyaluronic Acid, Sodium Benzoate, Sodium Levulinate, Potassium Sorbate, Sodium Phytate. User experienced was assessed by subjective participant self-reporting, and responses were collected at times users were able to confidently self-report significant results, ranging between 1-7 days of cream usage. Of this group, 100% reported the cream felt soothing on the skin, significantly reduced discomfort, irritation and itching, visibly reduced redness and inflammation, and left the skin appearing visibly more healthy.

The use of the terms "a," "an," "the," and similar referents in the context of describing the presently claimed invention (especially in the context of the claims) are to be construed to cover both the singular and the plural, unless otherwise indicated herein or clearly contracted by context. Recitation of ranges of values herein are merely intended to serve as a shorthand method of referring individually to each separate value falling within the range, unless otherwise indicated herein, and each separate value is incorporated into the specification as if it were individually recited herein. Use of the term "about" is intended to describe values either above or below the stated value in a range of approximately ±10%; in other embodiments the values may range in value either above or below the stated value in a range of approximately ±5%; in other embodiments the values may range in value either above or below the stated value in a range of approximately ±2%; in other embodiments the values may range in value either above or below the stated value in a range of approximately ±1%. The preceding ranges are intended to be made clear by context, and no further limitation is implied. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entireties. The present invention may be embodied in other specific forms without departing from the spirit or essential attributes thereof and, accordingly, reference should be made to the appended claims, rather than to the foregoing specification, as indicating the scope of the invention.

We claim:

1. A method for treating a nonviral, non-neoplastic topical skin condition in a mammal, comprising the steps of:
    (a) providing a composition consisting essentially of hemocyanin derived from organisms selected from the group consisting of:
    lobster species selected from *Nephrops novegicus, Homarus gammarus, Panularis elephas,* or *Homarus americanus,*
    crab species selected from *Carcinus maenas, Portunus pelagicus, Portunus trituberculatus, Callinectes sapidus, Cancer pagurus, Metacarcinus magister,* or *Chionoecetes;*
    crawfish species selected from *Procambarus clarkii* or *Procambarus zonangulus;* and
    shrimp species selected from *Penaeus monodon, Pandalus borealis, Acetes japonicas,* or *Trachysalambria curvirostris;*
    wherein hemocyanin is about 20% by weight based on the total weight of the composition; and
    (b) administering the composition to the mammal;
    whereby the nonviral, non-neoplastic topical skin condition is reduced.

2. The method of claim 1, wherein the hemocyanin is a recombinant protein or peptide.

3. The method of claim 1, wherein the composition is a topical composition administered topically to the skin daily for about 1 day to about 7 days.

4. The method of claim 1, wherein the composition contains a dosage of hemocyanin from about 25 ng to about 472 mg.

5. The method of claim 1, wherein the topical skin condition is selected from the group consisting of general dermatitis, atopic dermatitis, allergic contact dermatitis, seborrheic dermatitis, radiation dermatitis, radiation exposure irritation or rashes, xerosis, perioral dermatitis, stasis dermatitis, pregnancy-induced dermatitis, perineal dermatitis eczema, psoriasis, rosacea, pruritus, acne, rashes, sunburns, dermopathy, cercarial dermatitis, topical steroid withdrawal or use, redness or irritation care, erythema, papules, erosion, exudation, itching, redness, burning, stinging, swelling, rawness.

6. The method of claim 3, wherein the skin of the mammal is improved or soothed after the topical administering step.

7. The method of claim 3, wherein the skin of the mammal is reduced in itching or redness after the topical administering step.

8. The method of claim 3, wherein the skin of the mammal is reduced in irritation, burning, or stinging after the topical administering step.

9. The method of claim 3, wherein the skin inflammation of the mammal is reduced in erythema, papules, erosion, exudation, or rawness after the topical administering step.

10. A method for treating dry skin in a mammal not caused by a viral infection or a neoplasm, comprising the steps of:
    (a) providing a composition consisting essentially of hemocyanin wherein hemocyanin is about 20% by weight based on the total weight of the composition; and
    (b) administering the composition to the mammal;

whereby skin hydration or moisture content is increased and/or transepidermal water loss (TEWL) is decreased.

11. The method of claim 10, wherein hemocyanin is derived from organisms selected from the group consisting of lobsters, crabs, crawfish, shrimp, and arthropods.

12. The method of claim 11, wherein the organisms are selected from lobster species selected from the group consisting of *Nephrops novegicus, Homarus gammarus, Panularis elephas*, and *Homarus americanus*, or oyster species selected from the group consisting of *Crassostrea virginica* and *Ostrea edulis*, or crab species selected from the group consisting of *Carcinus maenas, Portunus pelagicus, Portunus trituberculatus, Callinectes sapidus, Cancer pagurus, Metacarcinus magister*, and *Chionoecetes*, or crawfish species selected from the group consisting of *Procambarus clarkii* and *Procambarus zonangulus*, or shrimp species selected from the group consisting of *Penaeus monodon, Pandalus borealis, Acetes japonicas*, and *Trachysalambria curvirostris*.

13. The method of claim 10, wherein the hemocyanin is a recombinant protein or peptide.

14. The method of claim 10, wherein the composition is a topical composition administered topically to the skin daily for about 1 day to about 7 days.

15. The method of claim 10, wherein the composition contains a dosage of hemocyanin from about 25 ng to about 472 mg.

16. The method of claim 14, wherein the skin of the mammal is improved or soothed after the topical administering step.

17. The method of claim 14, wherein the moisture content of the mammalian skin is increased after the topical administering step.

18. The method of claim 14, wherein the transepidermal water loss (TEWL) from the mammalian skin is decreased after the topical administering step.

* * * * *